US012709007B2

(12) United States Patent
Fogarty et al.

(10) Patent No.: US 12,709,007 B2
(45) Date of Patent: Aug. 18, 2026

(54) SURGICAL ROBOTIC SYSTEM WITH ACCESS PORT STORAGE

(71) Applicant: Covidien LP, Mansfield, MA (US)

(72) Inventors: Kevin R. Fogarty, Madison, CT (US); Andrew W. Zeccola, Salem, MA (US); Jared N. Farlow, Los Angeles, CA (US); Zachary T. Morgan, Boston, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/396,669

(22) Filed: Nov. 21, 2025

(65) Prior Publication Data

US 2026/0192448 A1 Jul. 9, 2026

Related U.S. Application Data

(63) Continuation of application No. 18/346,924, filed on Jul. 5, 2023, now Pat. No. 12,479,098.

(60) Provisional application No. 63/394,729, filed on Aug. 3, 2022.

(51) Int. Cl.

*B25J 9/16* (2006.01)
*A61B 34/30* (2016.01)
*A61B 34/37* (2016.01)

(52) U.S. Cl.

CPC ............. *B25J 9/1664* (2013.01); *A61B 34/37* (2016.02); *B25J 9/1692* (2013.01); *A61B 2034/302* (2016.02)

(58) Field of Classification Search

CPC ....... B25J 9/1664; B25J 9/1692; A61B 34/37; A61B 2034/302
USPC ................ 700/245–264; 318/568.11–568.25
See application file for complete search history.

(56) References Cited

U.S. PATENT DOCUMENTS 6,331,181 B1 * 12/2001 Tierney ................. G16H 40/63 606/130
9,085,083 B2 * 7/2015 Nixon .................... A61B 34/30
9,138,297 B2 * 9/2015 Brisson .................. A61B 34/30
2017/0105811 A1 * 4/2017 Garbus .................. A61B 90/98
2019/0076201 A1 * 3/2019 Wu ........................ A61B 34/20
2020/0163730 A1 * 5/2020 Chowaniec ............ A61B 90/36
2020/0268479 A1 * 8/2020 Garbus .................. A61B 34/25
2020/0405403 A1 * 12/2020 Shelton, IV ....... A61B 17/3421
2020/0405417 A1 * 12/2020 Shelton, IV ......... A61B 90/361
2021/0330405 A1 * 10/2021 Gonenc ................. B25J 9/0096
(Continued)

OTHER PUBLICATIONS

U.S. Prosecution File History of U.S. Appl. No. 18/346,924, filed Jul. 5, 2023, now issued as U.S. Pat. No. 12,479,098.

*Primary Examiner* — Wade Miles
*Assistant Examiner* — Sidney Leigh Molnar
(74) *Attorney, Agent, or Firm* — Carter, DeLuca & Farrell, LLP

(57) ABSTRACT

A surgical robotic system includes a robotic arm having an instrument drive unit and an access port configured to be secured to the robotic arm. The system also includes an instrument configured to couple to the instrument drive unit, where the instrument drive unit is configured to actuate the instrument. The system also includes a controller configured to: instruct the robotic arm to advance the instrument into the access port; instruct the instrument drive unit to calibrate the instrument inside the access port; determine a type of the access port during calibration of the instrument; and store the type of the access port in a memory.

18 Claims, 9 Drawing Sheets

(56) References Cited

U.S. PATENT DOCUMENTS

| | | | | |
|---|---|---|---|---|
| 2022/0096070 | A1* | 3/2022 | Vargas ............... | A61B 17/3421 |
| 2022/0096120 | A1* | 3/2022 | Bajo .................. | A61B 17/3421 |
| 2022/0096200 | A1* | 3/2022 | Vargas ............... | A61B 17/3415 |
| 2022/0104695 | A1* | 4/2022 | Russell .............. | A61B 1/00006 |
| 2022/0233261 | A1* | 7/2022 | Haraguchi ............. | A61B 90/50 |
| 2022/0415473 | A1* | 12/2022 | Bonaric ................. | A61B 34/30 |
| 2023/0165644 | A1* | 6/2023 | Deane .................. | A61B 1/0016<br>700/245 |
| 2023/0225812 | A1* | 7/2023 | Patel ...................... | A61B 90/16<br>700/245 |
| 2023/0320794 | A1* | 10/2023 | Scholan ................. | A61B 34/30<br>606/1 |
| 2024/0374330 | A1* | 11/2024 | Zeccola ................. | A61B 90/37 |
| 2024/0407865 | A1* | 12/2024 | Daniels .............. | A61B 18/1482 |
| 2025/0152276 | A1* | 5/2025 | Apostolopoulos ..... | A61B 90/90 |
| 2025/0235274 | A1* | 7/2025 | Mishra ................... | A61B 46/10 |

* cited by examiner

SURGICAL ROBOTIC SYSTEM WITH ACCESS PORT STORAGE

CROSS REFERENCE TO RELATED APPLICATIONS

This application is continuation of U.S. patent application Ser. No. 18/346,924, filed on Jul. 5, 2023, now U.S. Pat. No. 12,479,098, which claims the benefit of and priority to U.S. Provisional Patent Application Ser. No. 63/394,729 filed Aug. 3, 2022. The entire contents of each of the foregoing applications are incorporated by reference herein.

BACKGROUND

Surgical robotic systems are currently being used in minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Surgical robotic systems may be used with different types of access ports. Thus, there is a need for a system to determine and store information regarding access port type in the system.

SUMMARY

According to one embodiment of the present disclosure, a surgical robotic system is disclosed. The surgical robotic system includes a robotic arm having an instrument drive unit and an access port configured to be secured to the robotic arm. The system also includes an instrument configured to couple to the instrument drive unit, where the instrument drive unit is configured to actuate the instrument. The system also includes a controller configured to: instruct the robotic arm to advance the instrument into the access port; instruct the instrument drive unit to calibrate the instrument inside the access port; determine a type of the access port during calibration of the instrument; and store the type of the access port in a memory.

Implementations of the above embodiment may include one or more of the following features. According to one aspect of the above embodiment, the controller may be further configured to access the memory to check the type of the access port prior to determining the type of the access port. The controller may be also configured to determine whether the access port is attached to the robotic arm. The controller may be further configured to determine whether the instrument is coupled to the instrument drive unit. The controller may be also configured to instruct the robotic arm to advance the instrument into the access port based on determining whether the access port is attached to the robotic arm and whether the instrument is coupled to the instrument drive unit. The controller may be further configured to measure a parameter of the access port during calibration of the instrument. The controller may be additionally configured to compare the parameter with threshold stored in the memory and to determine the type of the access port based on a comparison of the parameter with the threshold. The parameter may be indicative of at least one of diameter or length of the access port. The parameter may be at least one of pitch limit, yaw limit, or jaw angle limit.

According to another embodiment of the present disclosure, a method for controlling a surgical robotic system is disclosed. The method includes instructing a robotic arm to advance an instrument into an access port. The robotic arm includes an instrument drive unit configured to couple to the instrument and to actuate the instrument, and the robotic arm is further configured to secure the access port. The method also includes instructing the instrument drive unit to calibrate the instrument inside the access port, determining a type of the access port during calibration of the instrument, and storing the type of the access port in a memory.

Implementations of the above embodiment may include one or more of the following features. According to one aspect of the above embodiment, the method may also include accessing the memory to check the type of the access port prior to determining the type of the access port. The method may further include determining whether the access port is attached to the robotic arm. The method may additionally include determining whether the instrument is coupled to the instrument drive unit. The method may also include instructing the robotic arm to advance the instrument into the access port based on determining whether the access port is attached to the robotic arm and whether the instrument is coupled to the instrument drive unit. The method may further include determining a parameter of the access port during calibration of the instrument. The method may additionally include comparing the parameter with threshold stored in the memory and to determine the type of the access port based on a comparison of the parameter with the threshold. The parameter may be indicative of at least one of diameter or length of the access port. The parameter may be at least one of pitch limit, yaw limit, or jaw angle limit.

According to a further embodiment of the present disclosure, a surgical robotic system is disclosed. The surgical robotic system includes a robotic arm, an instrument drive unit, and an access port configured to be secured to the robotic arm. The system also includes an instrument configured to couple to the instrument drive unit, where the instrument drive unit is configured to actuate the instrument. The system further includes a controller configured to: determine whether the access port is attached to the robotic arm and whether the instrument is coupled to the instrument drive unit; instruct the robotic arm to advance the instrument into the access port based on determining whether the access port is attached to the robotic arm and whether the instrument is coupled to the instrument drive unit; instruct the instrument drive unit to calibrate the instrument inside the access port; determine a type of the access port during calibration of the instrument; and store the type of the access port in a memory.

Implementations of the above embodiment may include one or more of the following features. According to one aspect of the above embodiment, the controller may be further configured to access the memory to check the type of the access port prior to determining the type of the access port.

BRIEF DESCRIPTION OF THE DRAWINGS

Various embodiments of the present disclosure are described herein with reference to the drawings wherein.

DETAILED DESCRIPTION

Figure 1:
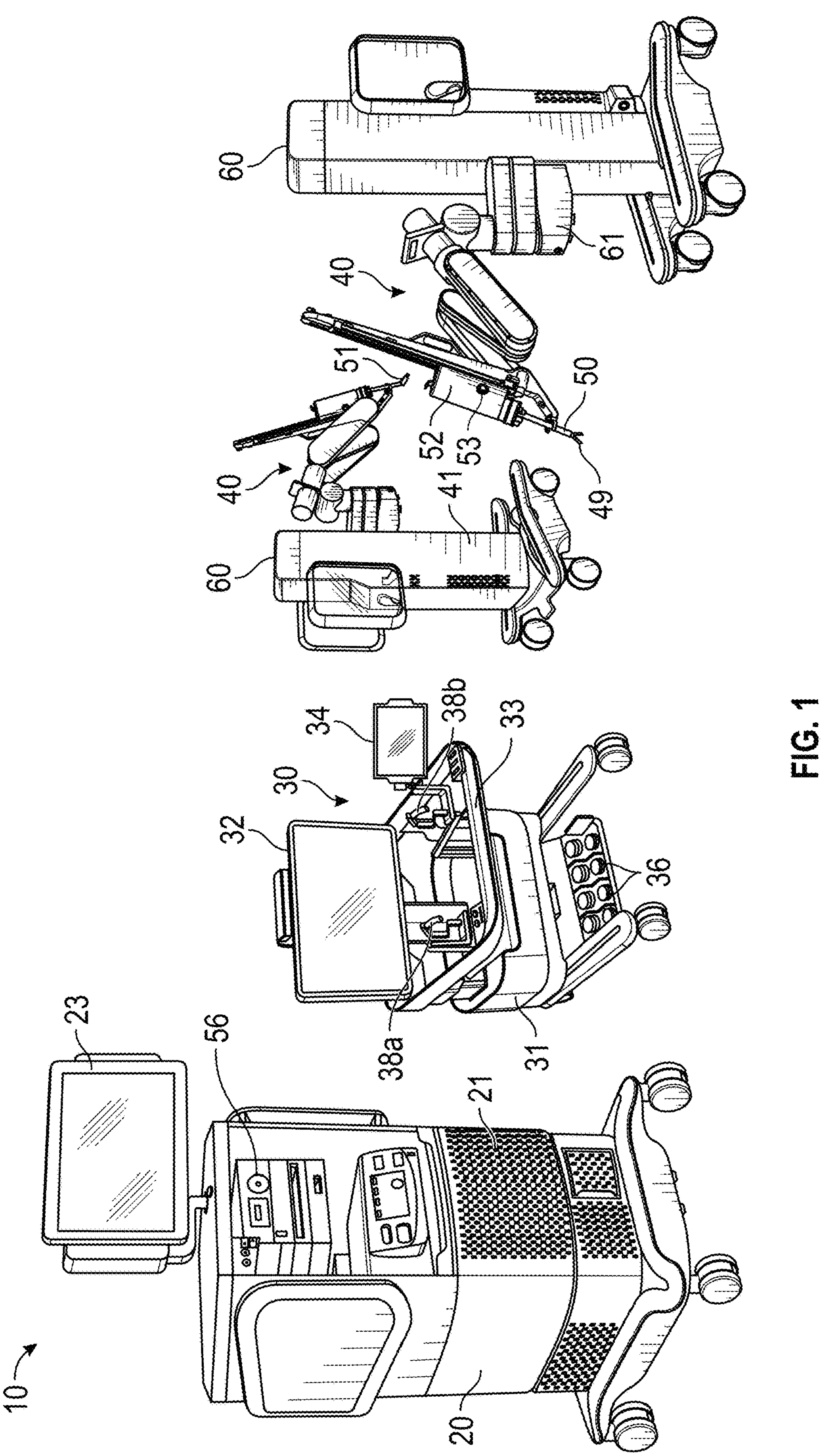
FIG. 1 is a schematic illustration of a surgical robotic system including a control tower, a console, and one or more surgical robotic arms each disposed on a movable cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices, which are processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 removably coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include an endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 of the surgical instrument 50 disposed on the robotic arm 40, and a second display 34, which displays a user interface for controlling the surgical robotic system 10. The first display 32 and second display 34 may be touchscreens allowing for displaying various graphical user inputs.

The surgeon console 30 also includes a plurality of user interface devices, such as foot pedals 36 and a pair of handle controllers **38*a* and 38*b* which are used by a user to remotely control robotic arms 40. The surgeon console further includes an armrest 33 used to support clinician's arms while operating the handle controllers 38*a* and 38*b***.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers **38*a* and 38*b*. The foot pedals 36 may be used to enable and lock the hand controllers 38*a* and 38*b*, repositioning camera movement and electrosurgical activation/deactivation. In particular, the foot pedals 36 may be used to perform a clutching action on the hand controllers 38*a* and 38*b*. Clutching is initiated by pressing one of the foot pedals 36, which disconnects (i.e., prevents movement inputs) the hand controllers 38*a* and/or 38*b* from the robotic arm 40 and corresponding instrument 50 or camera 51 attached thereto. This allows the user to reposition the hand controllers 38*a* and 38*b* without moving the robotic arm(s) 40 and the instrument 50 and/or camera 51**. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
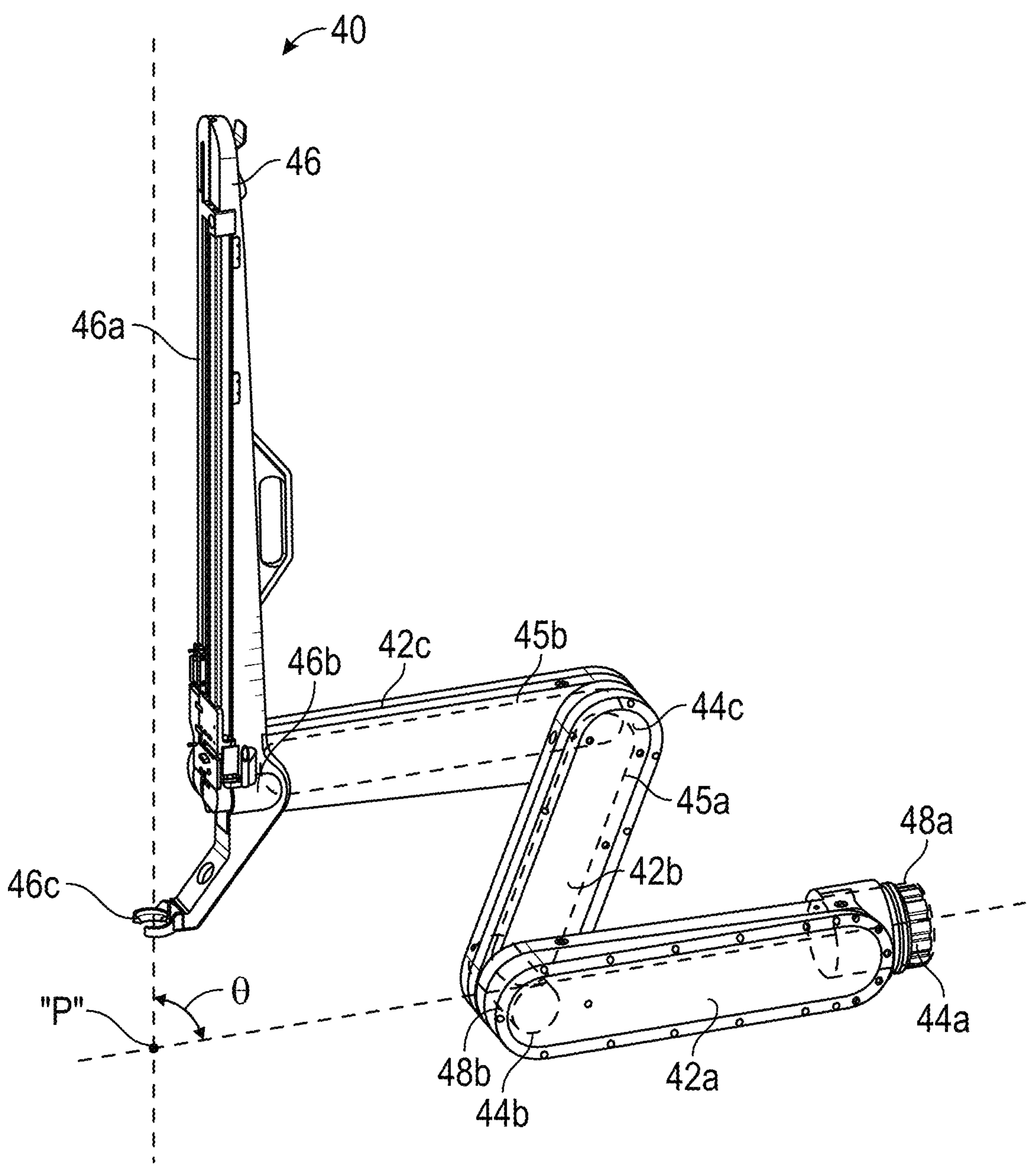
FIG. 2 is a perspective view of a surgical robotic arm of the surgical robotic system of FIG. 1 according to an embodiment of the present disclosure.
Figure 3:
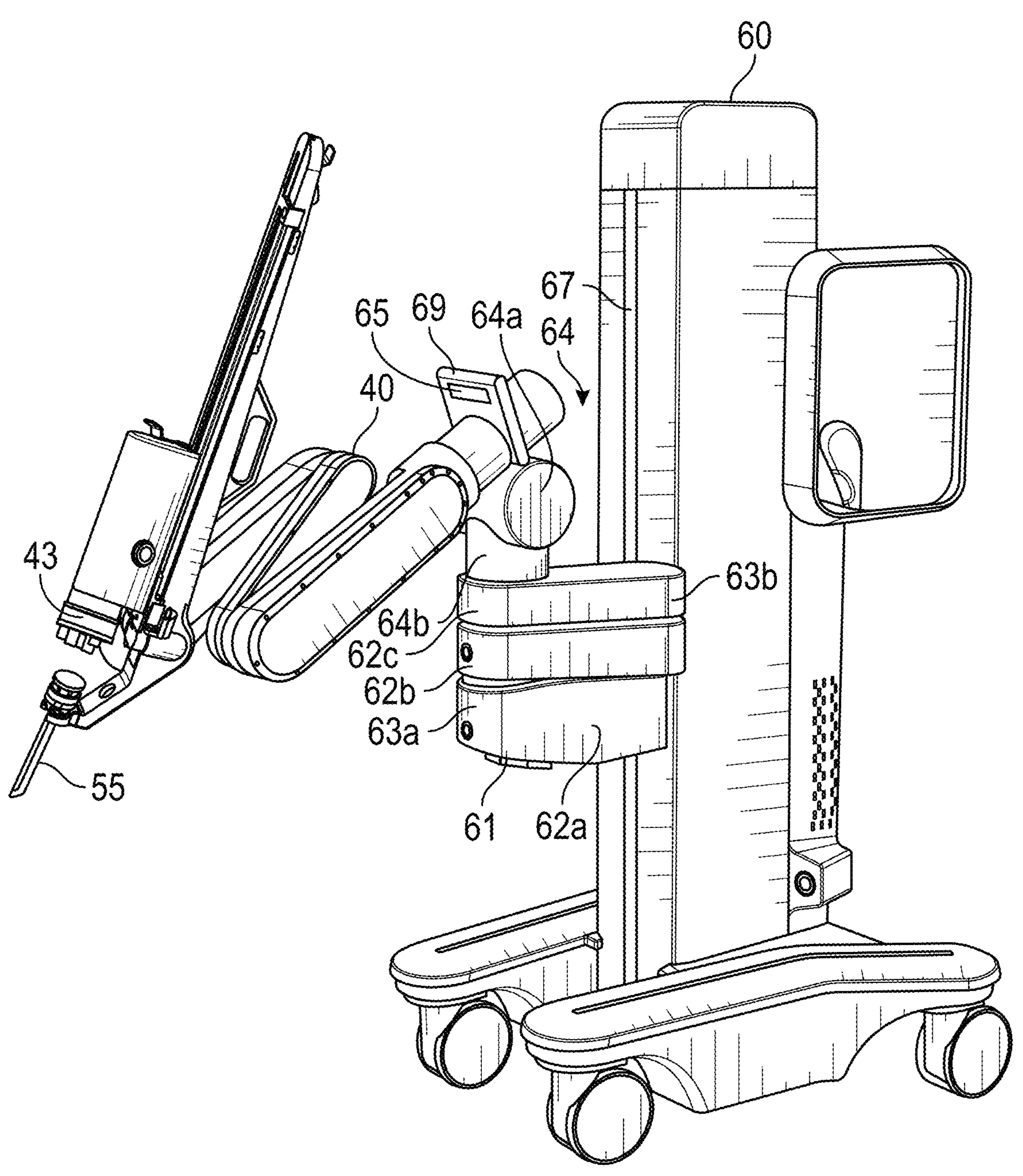
FIG. 3 is a perspective view of a movable cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the movable cart 60 and defines a first longitudinal axis. With reference to FIG. 3, the movable cart 60 includes a lift 67 and a setup arm 61, which provides a base for mounting of the robotic arm 40. The lift 67 allows for vertical movement of the setup arm 61. The movable cart 60 also includes a display 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components an end effector 49 of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
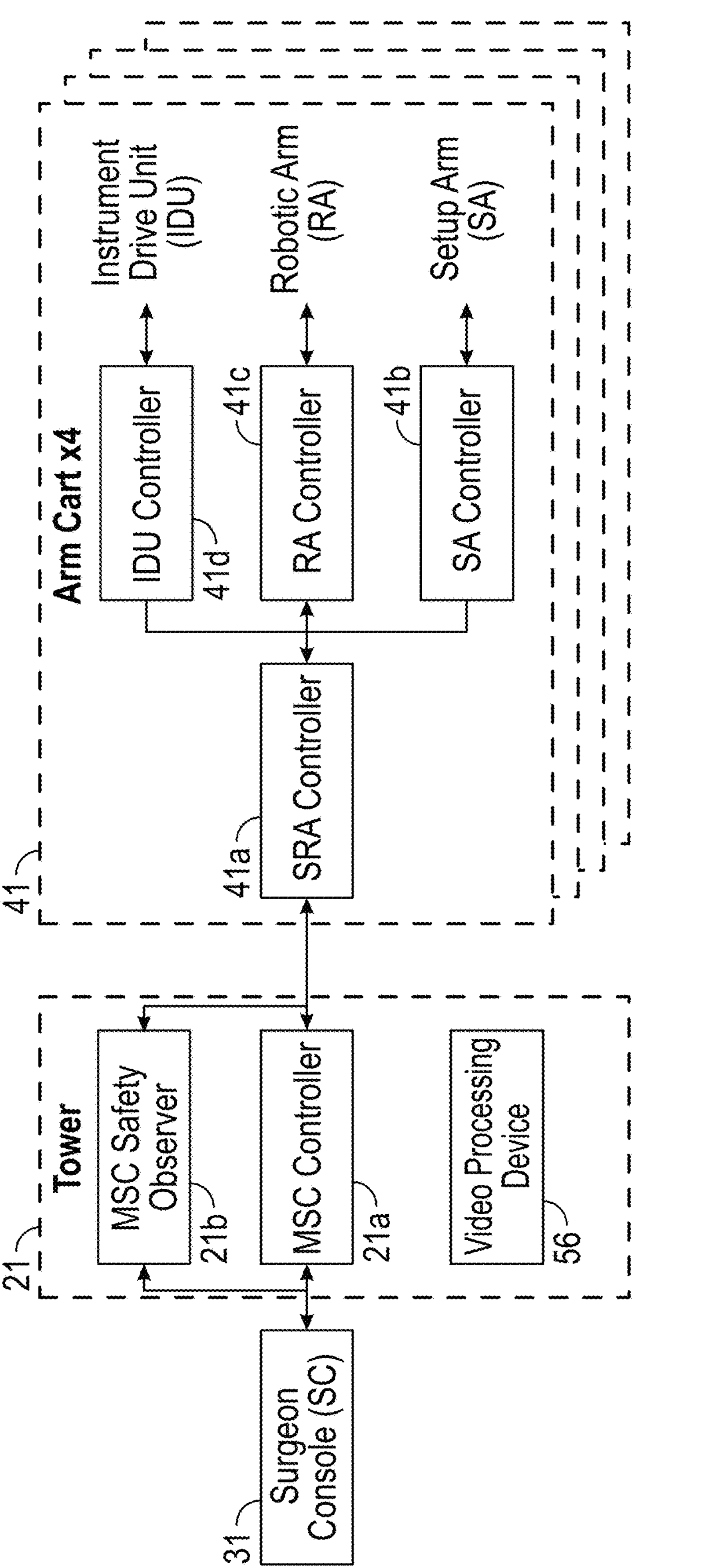
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controllers 38*a* may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38*a* is then scaled by a scaling function executed by the controller 21*a*. In embodiments, the coordinate position may be scaled down and the orientation may be scaled up by the scaling function. In addition, the controller 21*a* may also execute a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
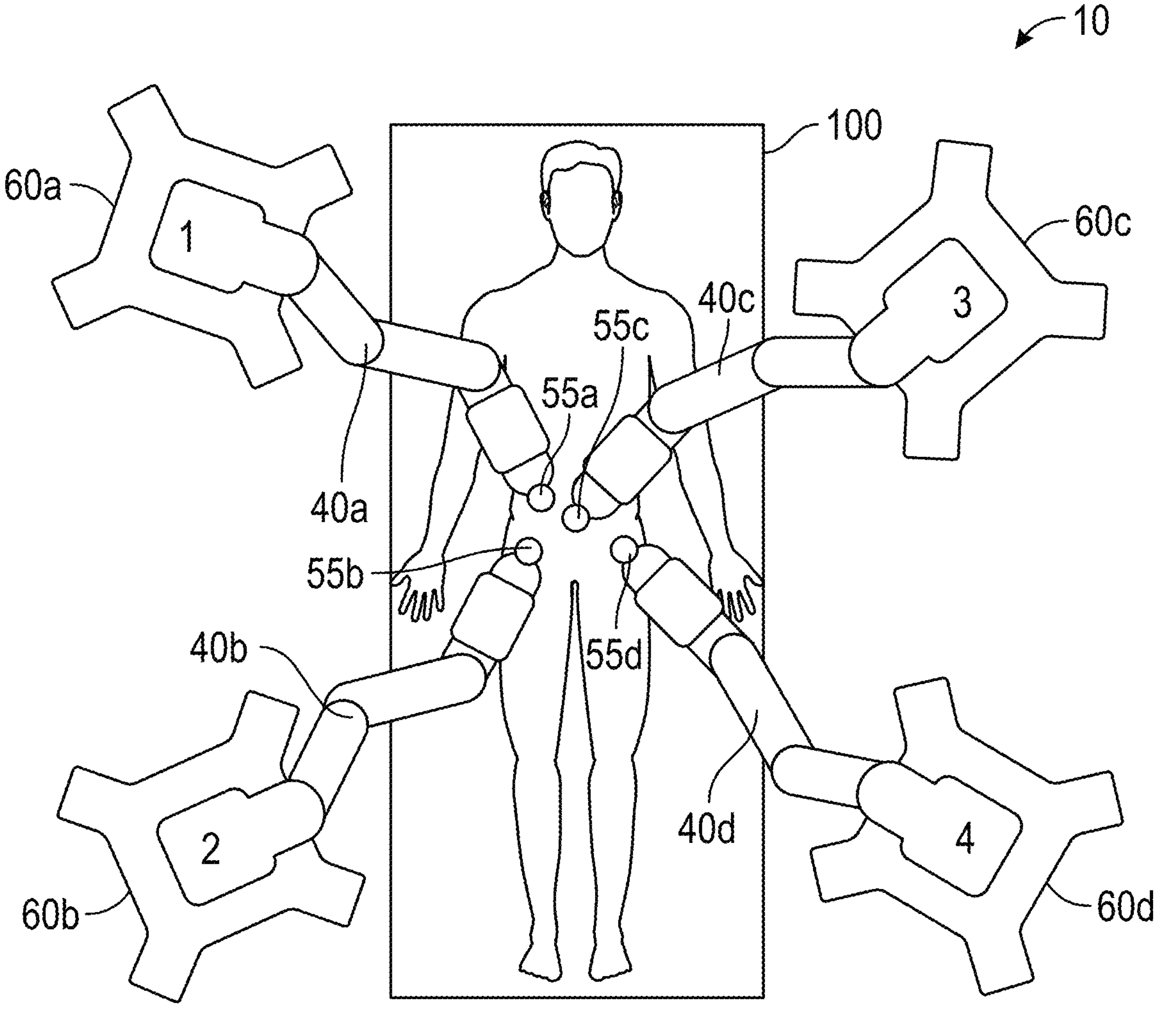
FIG. 5 is a plan schematic view of movable carts of FIG. 1 positioned about a surgical table according to an aspect of the present disclosure.

With reference to FIG. 5, the surgical robotic system 10 is setup around a surgical table 100. The system 10 includes movable carts 60*a-d*, which may be numbered "1" through "4." During setup, each of the carts 60*a-d* are positioned around the surgical table 100. Position and orientation of the carts 60*a-d* depends on a plurality of factors, such as placement of a plurality of access ports 55*a-d*, which in turn, depends on the surgery being performed. Once the port placement is determined, the access ports 55*a-d* are inserted into the patient, and carts 60*a-d* are positioned to insert instruments 50 and the endoscopic camera 51 into corresponding ports 55*a-d*.

Figure 6:
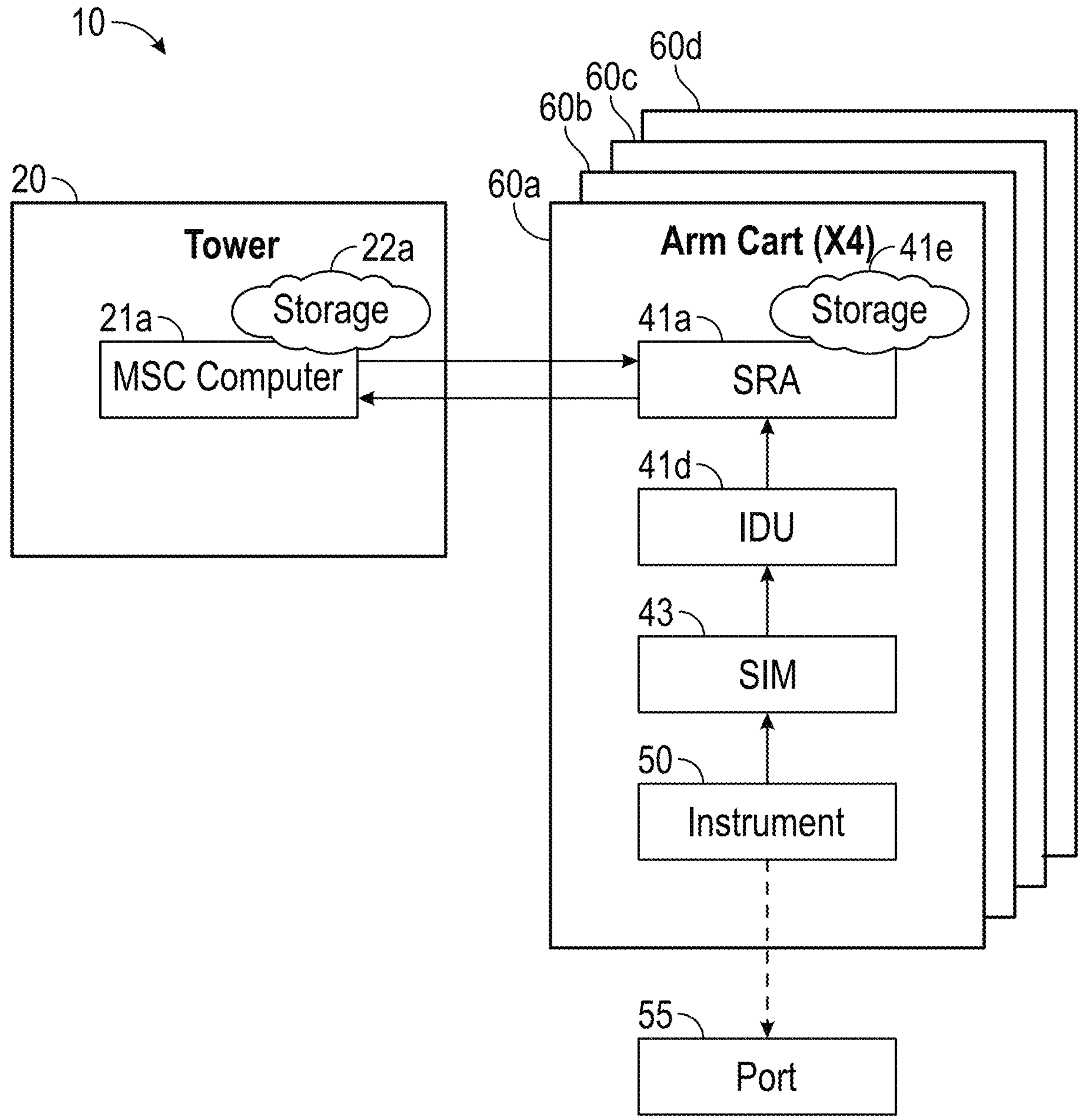
FIG. 6 is a schematic diagram of a computer architecture of the surgical robotic system, the robotic, arm and the access port according to an embodiment of the present disclosure.

FIG. 6 shows a schematic diagram of the control tower 20 and the mobile carts 60*a-d*. The control tower 20 includes the controller 21*a* and a storage 22*a*, which may be non-transitory computer-readable medium configured to store any suitable computer data, such as software instructions executable by the controller 21*a*. The controller 21*a* also includes transitory memory 22*b* (FIG. 9) for loading instructions and other computer readable data during execution of the instructions. As described above with respect to FIG. 4, the controller 21*a* is in communication with the main cart controller 41*a*, the IDU controller 41*d*, a sterile interface module (SIM) 43, and the instrument 50. The main cart controller 41*a* is also coupled to a storage 41*e*, which is configured to store any suitable computer data, such as software instructions executable by the controller 41*a*.

During use, each of the robotic arms 40*a-d* is attached to one of the access ports 55*a-d* (generally shown as access port 55 in FIG. 6) that is inserted into the patient by attaching the latch 46*c* (FIG. 2) to the access port 55 (FIG. 3). The IDU 52 is attached to the holder 46, followed by the SIM 43 being attached to a distal portion of the IDU 52. Thereafter, the instrument 50 is attached to the SIM 43. The instrument 50 is then inserted through the access port 55 by moving the IDU 52 along the holder 46. The SIM 43 includes a plurality of drive shafts configured to transmit rotation of individual motors of the IDU 52 to the instrument 50 thereby actuating the instrument 50. In addition, the SIM 43 provides a sterile barrier between the instrument 50 and the other components of robotic arm 40, including the IDU 52. The SIM 43 is also configured to secure a sterile drape (not shown) to the IDU 52.

Figure 7:
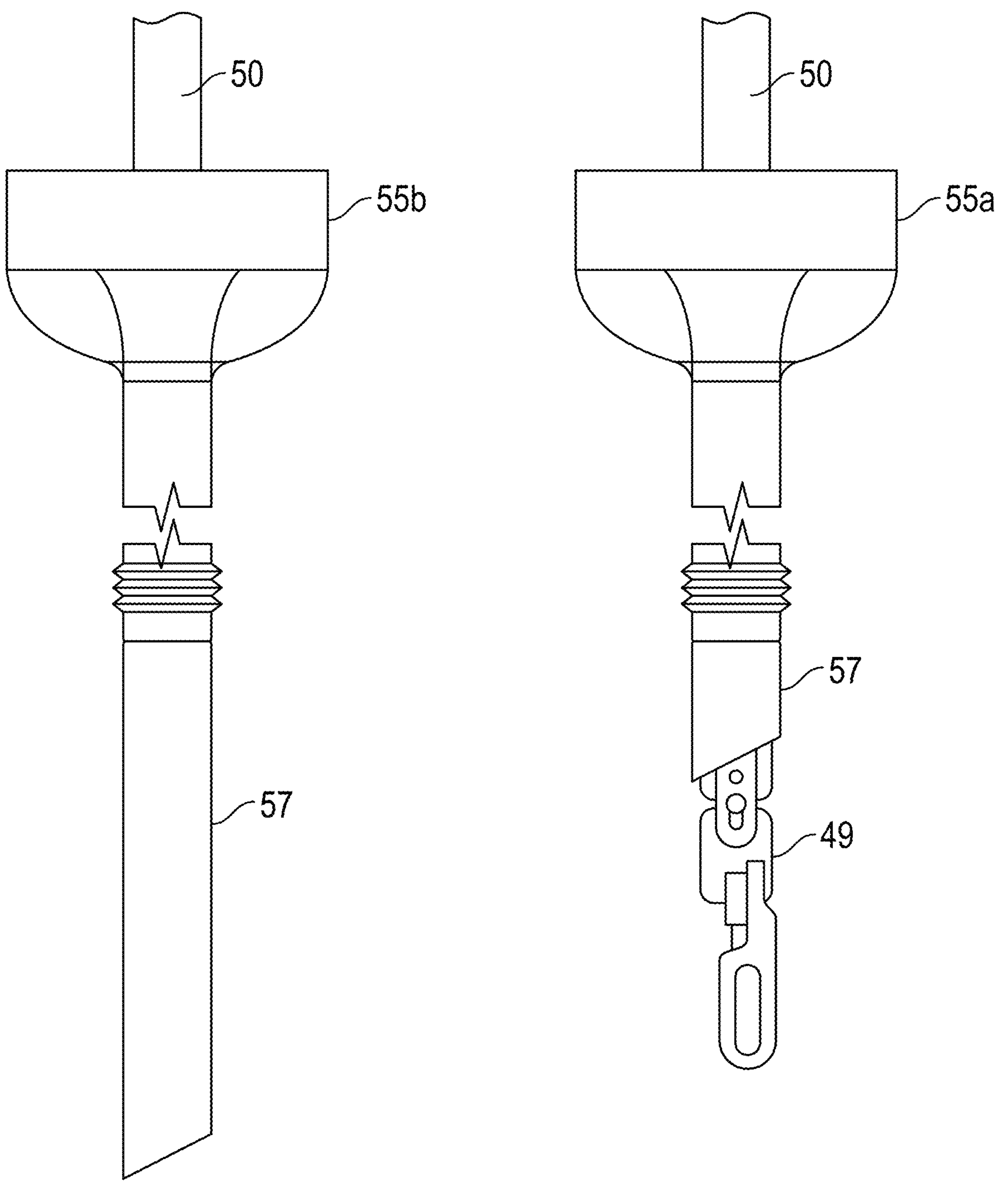
FIG. 7 is a side view of access ports of different lengths according to the present disclosure.

With reference to FIG. 7, each of the access ports 55*a-d* may include a storage device and a communication device configured to establish wired and/or wireless communications with the IDU 52, e.g., through the instrument 50 and the SIM 43. Thus, the access ports 55*a-d* are configured to communicate with the main cart controller 41*a*.

As shown in FIG. 7, during surgery, ports of different types, which have different dimensions (e.g., diameter and lengths) may be used, in particular, the access port 55*a* may be standard length access ports having a length of from about 100 mm to about 200 mm, whereas the access ports 55*b* are longer and may have a length of 200 mm or above and may be used for bariatric surgery. Port diameter may be from about 8 mm to about 15 mm.

The system 10 is configured to differentiate between different types of access ports 55, namely, based on properties, such as length (e.g., standard vs. long), material, (e.g., metal vs. plastic), and diameter (e.g., 8 mm, 11 mm, 12 mm, or 15 mm). Access ports 55 may include any combination of the properties.

Figure 8:
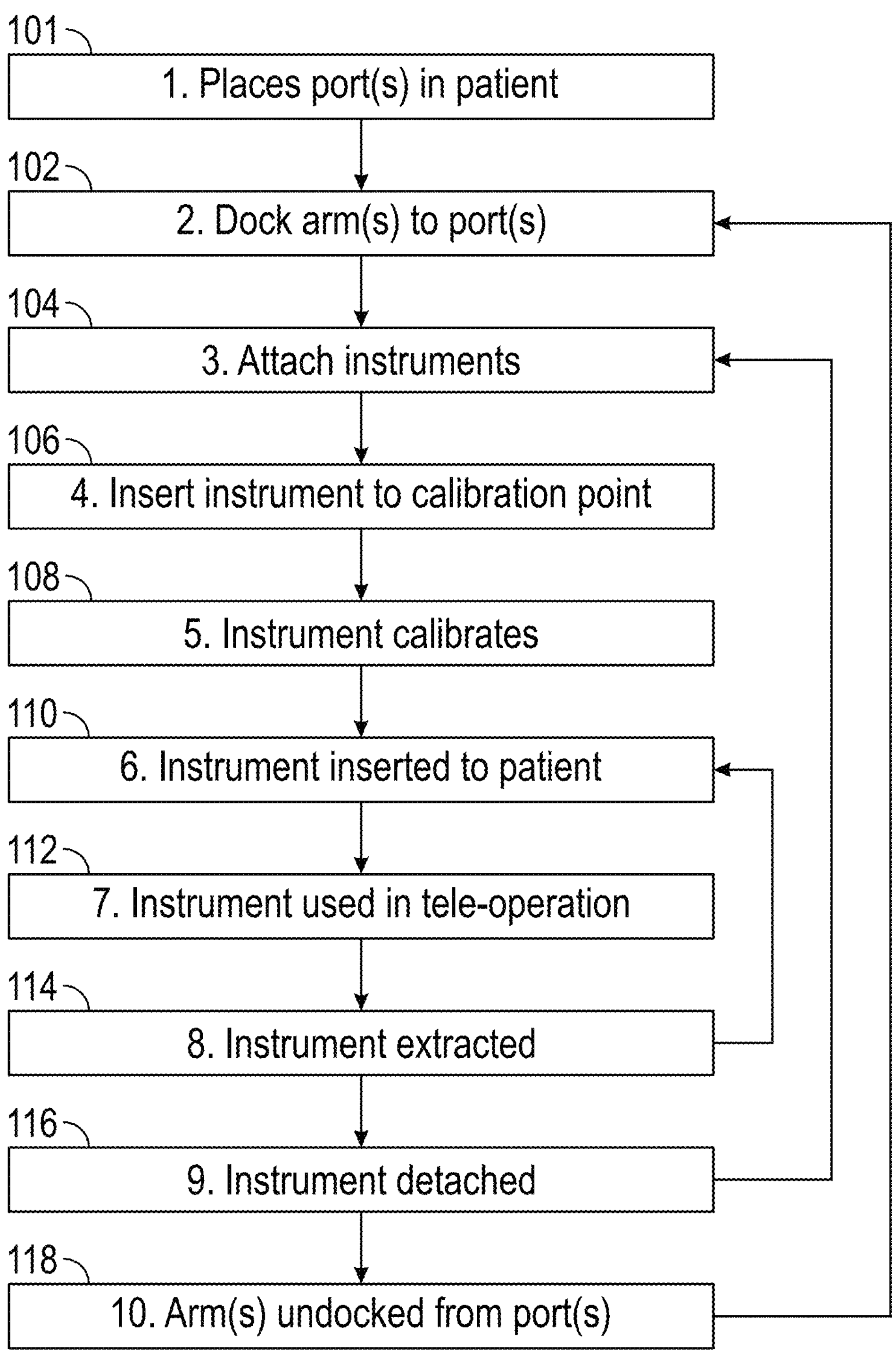
FIG. 8 is a flow chart of a method of using the surgical robotic system of FIG. 1 according to an embodiment of the present disclosure.

FIG. 8 shows a method of use of the surgical robotic system 10. Some or all the steps of the method of FIG. 8 may be performed by a user interacting with the system 10 or by the system 10 in automated manner. User guidance may be provided by a graphical user interface (GUI) displayed on any of the displays 23, 32, 34 of the system 10. In addition, the GUI may progress through a series of frames or instructions associated with each of the steps by receiving confirmations from the system 10 (e.g., sensor signals, user input, etc.)

At step 101, the access ports 55*a-d* are inserted into the patient based on preset locations, which may be determined during surgical planning. At step 102, the mobile carts 60*a-d* are positioned, e.g., wheeled next to the surgical table 100 and each of the robotic arms 40*a-d* via the respective latches 46*c* is attached to the inserted access ports 55*a-d*. At step 104, the instruments 50 and camera 51 are coupled to the respective IDU 52 and are then inserted into the access ports 55*a-d*. At step 106, as the instruments 50 are inserted into their respective ports 55*a-d* and at step 108, the instrument 50 are calibrated, which may include moving the end effector 49 about each degree of freedom (e.g., pitch, yaw, jaw angle, rotation of the entire instrument, etc.) until a mechanical limit or another setpoint is reached. Diameter is determined by moving the end effector 49 until the mechanical limits are reach at end of travel at both end of the movement arc. Length is determined by moving the end effector 49 through the access port 55 and tapping the inner walls of the access port 55 until no physical obstruction, i.e., access port 55, is detected. The material of the access port 55 may be determined during calibration as well as the torque values are different when the end effector 49 contacts different materials.

Mechanical limits may be determined by measuring torque of the motor(s) of the IDU 52. In particular, a sharp increase in, i.e., spiking, torque is indicative of encountering a mechanical limit by the end effector 49. After calibration, at step 110, the instruments 50 are inserted into patient by moving the IDU 52 along the sliding mechanism 46*a* of the robotic arm 40. At step 112, the instruments 50 along with the camera 51 are used in teleoperation to perform the surgical procedure(s) on the patient.

After completion of the surgery, at step 114, the instruments 50 and the camera 51 are extracted (e.g., via the sliding mechanism 46*a* of the robotic arm 40*a-d*.) At step 116, the instruments 50 are detached from the IDU 52 and at step 118, the robotic arms 40*a-d* are uncoupled from the access ports 55*a-d*.

Figure 9:
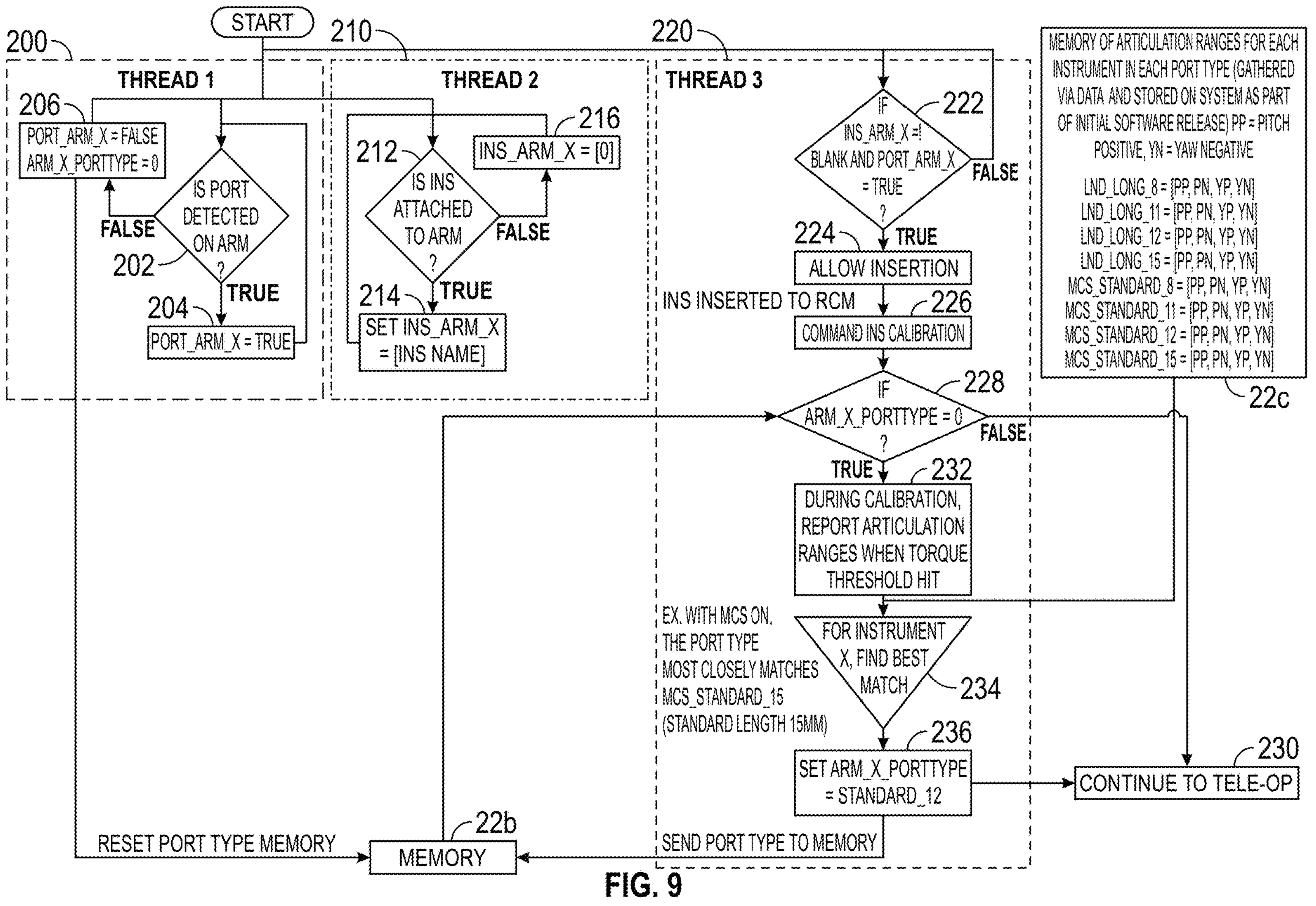
FIG. 9 is a flow chart of a method of access port management according to an embodiment of the present disclosure.

FIG. 9 shows a method of access port data management, which includes three threads, which may be executed in parallel, concurrently, or series. The threads may be embodied as software instructions executable by any controller of the surgical robotic system 10, e.g., controller 21*a*, 41*a*, etc. A first thread 200 may include continuously checking port connection status and storing the same in the memory 22*b* of the controller 21*a*. The memory 22*b* may store a port connection status, e.g., Boolean, reflective of the connection status of the access port 55*a-d* to the latch 46*c* of one of the robotic arms 40*a-d*. Access port status may be determined by using a contact switch or any other suitable mechanism to determine whether the latch 46*c* is engaged to one of the access ports 55*a-d*. The memory 22*b* may also store a port type, e.g., standard, long, etc., and may also include one or more parameters describing the type of the access ports 55*a-d*. Port type parameters may include length, diameter, material type, and other parameters. If one of the access ports 55*a-d* is detached, then the port type may be changed to indicate that no access port 55*a-d* is attached, e.g., changed to 0.

A second thread 210 may include continuously checking instrument connection status and storing the same in the memory 22*b* of the controller 21*a*. The memory 22*b* may store an instrument connection status reflective of the connection status of the instrument 50 attached to one of the robotic arms 40*a-d*, i.e., whether the instrument 50 is coupled to the IDU 52. The instrument status may be determined based on an identifier transmitted by the instrument 50 to the IDU 52 after the instrument 50 is coupled to the IDU 52. The instrument connection status may include the instrument name or a null indicator (e.g., none, 0, etc.).

A third thread 220 may be used to enable insertion of the instrument 50 based on the instrument connection status and the port connection status. Thus, if both are true, the controller 21*a* enables insertion of the instrument 50. The third thread may be also configured to determine the type of the access port 55*a-d* based on calibration data by comparing mechanical limits to access port dimensions and material type. Parameters may be stored in a look-up table 22*c* or any other database stored in the storage 22*a*. In particular, the controller 21*a* compares one or more of the calibration values, e.g., positive/negative pitch and yaw, and to a stored value range based on the type of the instrument 50. The controller 21*a* then determines the type of the access port, e.g., diameter and length dimensions, material type, based on the calibration data of the instrument 50. The controller 21*a* and/or controller 41*a* save the port type in the storage 22*a* or 41*e*. The port type is used by the controller 21*a* until the access port 55 is removed.

With continued reference to FIG. 9, the first thread 200 includes determining port connection status at step 202, i.e., whether the access port 55 is attached to the robotic arm 40. Access port status may be determined by using a contact switch or any other suitable mechanism to determine whether the latch 46*c* is engaged to one of the access ports 55*a-d*. At step 204, if the access port 55 is attached, the controller 21*a* sets the port connection status to true and returns to step 202 to continuously determine whether the access port 55 is attached. At step 206, if no access port 55 is attached, the controller 21*a* sets the port connection status to false and also resets the port type value.

The second thread 210 includes determining instrument connection status at step 212, i.e., whether the instrument 50 is coupled to the IDU 52. The instrument status may be determined based on an identifier transmitted by the instrument 50 to the IDU 52 after the instrument 50 is coupled to the IDU 52. In embodiments, the instrument 50 may include a wireless or a wired interface with the IDU 52 and the instrument 50 may communicate various instrument parameters and identifiers (e.g., name, model, serial no., etc.) to the IDU 52 and to the controllers 21*a* and/or 41*a* (see FIG. 6).

At step 214, if the controller 21*a* and/or 41*a* receives an identifier of the instrument 50 indicative that the instrument 50 is coupled to the IDU52, the controller 21*a* sets the instrument connection status to the instrument name or another other designator indicating the instrument type and connection status and reverts to step 214 to continuously check instrument status. If no connection between the instrument 50 and the IDU 52 is detected, at step 216, the instrument connection status is updated to reflect lack of the connection, e.g., null indicator, none, 0, etc.

The third thread 220 controls insertion, calibration, and enables teleoperation of the instrument 50. At step 222, the controller 21*a* verifies access port connection status and instrument connection status. If one of the statuses is negative, i.e., either the access port 55 or the instrument 50 is not attached, then the method proceeds to the first and/or second threads 200 and 210 until both connection statuses are confirmed.

Once the instrument 50 and the access port 55 are confirmed as connected, at step 224, the controller 21*a* enables insertion of the instrument 50 by the IDU 52 being moved along the sliding mechanism 46*a* of the robotic arm 40. Insertion may be commenced in response to user input.

During insertion, at step 226, calibration of the instrument 50 and the end effector 49 is commenced and at step 228, the controller 21*a* verifies whether the port type value is set to a null value, e.g., 0, before proceeding. If the port type value already stores the access port type, then the process proceeds to step 230, and teleoperation of the robotic arm 40 is enabled. This situation occurs when the access port type was previously detected by the system 10 as described below in steps 232-236 and avoids determination the type of the access port 55 during calibration, thereby minimizing insertion time of the instrument 50.

If the port type value is set to null, then the method proceeds to calibration, which includes moving the end effector 49 inside a cannula 57 of the access port 55 until a mechanical limit is encountered by the end effector 49 hitting the interior of the cannula 57 of the access port 55. During calibration, at step 232, the controller 21*a* may record a plurality of values, such as positive and negative limits for each of the degrees of freedom, e.g., pitch positive, pitch negative, yaw positive, yaw negative, zero jaw angle position, jaw angle maximum, etc. In addition, the instrument 50 may be continuously advanced through the cannula 57 tapping against the inner wall to determine when the cannula 57 ends, thereby determining the length of the access port 55.

At step 234, the controller 21*a* compares the calibration values to the end effector articulation ranges in the look-up table 22*c*. In particular, the look-up table 22*c* may store articulation ranges for any of the instruments 50 usable by the system 10 in each access port type. The controller 21*a* selects or identifies the access port type based on the match of the calibration values with the articulation ranges. At step 236, the controller 21*a* sets the port type as the matched access port type and saves the port type in the memory 22*b*. Once the access port type is set, the controller 21*a* proceeds to step 230 and enables teleoperation of the robotic arm 40.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:

a robotic arm including an instrument drive unit;

an access port configured to be secured to the robotic arm;

an instrument configured to couple to the instrument drive unit, wherein the instrument drive unit is configured to actuate the instrument;

a memory configured to store data including data associated with the access port; and a controller configured to:

access the memory to determine whether data stored in the memory includes a value indicative of a type of the access port;

when the data stored in the memory includes the value indicative of the type of the access port, use the value as the type of the access port; and when the data stored in the memory does not include the value indicative of the type of the access port, instruct the robotic arm to advance the instrument into the access port and instruct the instrument drive unit to perform calibration of the instrument to determine the type of the access port based on the calibration of the instrument, and store the value indicative of the type of the access port in the memory.

2. The surgical robotic system according to claim 1, wherein the calibration includes actuating the instrument inside the access port through at least one degree of freedom to determine at least one mechanical limit encountered by the instrument contacting an interior surface of the access port.

3. The surgical robotic system according to claim 2, wherein the controller is further configured to determine a type of the access port based on the at least one mechanical limit determined during calibration of the instrument.

4. The surgical robotic system according to claim 1, wherein the controller is further configured to determine whether the access port is attached to the robotic arm.

5. The surgical robotic system according to claim 4, wherein the controller is further configured to instruct the robotic arm to advance the instrument into the access port based on determining when the access port is attached to the robotic arm.

6. The surgical robotic system according to claim 1, wherein the controller is further configured to measure a parameter of the access port during calibration of the instrument.

7. The surgical robotic system according to claim 6, wherein the controller is further configured to compare the parameter with a threshold stored in the memory and to determine the type of the access port based on a comparison of the parameter with the threshold.

8. The surgical robotic system according to claim 6, wherein the parameter is indicative of at least one of diameter or length of the access port.

9. The surgical robotic system according to claim 6, wherein the parameter is at least one of pitch limit, yaw limit, or jaw angle limit.

10. A method for controlling a surgical robotic system, the method comprising:

accessing a memory configured to store data associated with an access port to determine whether data stored in the memory includes a value indicative of a type of the access port;

when the data stored in the memory includes the value indicative of the type of the access port, using the value as the type of the access port; and when the data stored in the memory does not include the value indicative of the type of the access port, instructing a robotic arm to advance an instrument into the access port and instructing an instrument drive unit to perform calibration of the instrument to determine the type of the access port based on the calibration of the instrument, and storing the value indicative of the type of the access port in the memory.

11. The method according to claim 10, wherein calibrating the instrument includes actuating the instrument inside the access port through at least one degree of freedom to determine at least one mechanical limit encountered by the instrument contacting an interior surface of the access port.

12. The method according to claim 11, further comprising determining the type of the access port based on the at least one mechanical limit determined during calibration of the instrument.

13. The method according to claim 11, further comprising determining whether the access port is secured to the robotic arm.

14. The method according to claim 13, further comprising instructing the robotic arm to advance the instrument into the access port based on determining when the access port is secured to the robotic arm.

15. The method according to claim 10, further comprising measuring a parameter of the access port during calibration of the instrument.

16. The method according to claim 15, further comprising comparing the parameter with a threshold stored in the memory and determining the type of the access port based on a comparison of the parameter with the threshold.

17. The method according to claim 15, wherein the parameter is indicative of at least one of diameter or length of the access port.

18. The method according to claim 15, wherein the parameter is at least one of pitch limit, yaw limit, or jaw angle limit.

* * * * *